United States Patent
Kahre et al.

(10) Patent No.: US 6,641,803 B1
(45) Date of Patent: Nov. 4, 2003

(54) HAIR-CONDITIONING AGENTS

(75) Inventors: Joerg Kahre, Leichlingen (DE); Norbert Boyxen, Kempen (DE); Celia Kosboth, Duisburg (DE); Dagmar Goebels, Voerde (DE); Werner Seipel, Hilden (DE)

(73) Assignee: Cognis Deutschland GmbH & Co. KG, Dusseldorf (DE)

( * ) Notice: Subject to any disclaimer, the term of this patent is extended or adjusted under 35 U.S.C. 154(b) by 0 days.

(21) Appl. No.: 09/601,672

(22) PCT Filed: Jan. 28, 1999

(86) PCT No.: PCT/EP99/00563
§ 371 (c)(1),
(2), (4) Date: Dec. 21, 2000

(87) PCT Pub. No.: WO99/39690
PCT Pub. Date: Aug. 12, 1999

(30) Foreign Application Priority Data

Feb. 6, 1998 (DE) ............................... 198 05 703

(51) Int. Cl.⁷ ..................... A61K 7/50; A61K 7/00
(52) U.S. Cl. ............... 424/70.1; 424/70.1; 424/401; 536/18.5; 536/18.6; 536/4.1; 536/124
(58) Field of Search ............... 424/70.1, 401; 536/18.5, 18.6, 4.1, 124

(56) References Cited

U.S. PATENT DOCUMENTS

| | | | | |
|---|---|---|---|---|
| 4,172,887 A | 10/1979 | Vanlerberghe et al. | ......... | 427/70 |
| 5,374,716 A | 12/1994 | Biermann et al. | ......... | 536/18.5 |
| 5,576,425 A | 11/1996 | Hill et al. | ......... | 536/18.6 |
| 5,718,891 A | 2/1998 | Prat et al. | ......... | 424/70.28 |

FOREIGN PATENT DOCUMENTS

| | | |
|---|---|---|
| DE | 1 165 574 | 3/1964 |
| DE | 20 24 051 | 12/1971 |
| DE | 43 08 794 | 4/1994 |
| DE | 196 51 447 | 10/1997 |
| DE | 197 08 133 | 12/1997 |
| DE | 196 52 302 | 3/1998 |
| EP | 0 301 298 | 2/1989 |
| FR | 2 252 840 | 6/1975 |
| GB | 962 919 | 7/1964 |
| GB | 1 333 475 | 10/1973 |
| WO | WO90/03977 | 4/1990 |
| WO | WO91/01295 | 2/1991 |
| WO | WO97/47284 | 12/1997 |

OTHER PUBLICATIONS

Kahre et al. (CA 128:92980, CAPLUS, abstract of WO 9747284).*

R.Puchta et al, *A New Generation of Softeners*, Tenside Surf. Det. 30 p. 186, 189–191 (1993).

M.Brock, *Neue Entwicklungen auf dem Gebiet der Waescheweichspueler*, Tens. Surf. Det. 30 p. 394,396,398 (1998).

R.Lagerman et al., *Synthesis and Performance of Ester Quaternary Biodegradable Softeners*, J. Am. Oil Chem.Soc. 71 p. 97 (1994).

I.Shapiro et al., *Environmentally Friendly Ester Quats*, Cosm. Toil 109 p. 77 (1994).

Finkel, *Formulierung kosmetischer Sonnenschutzmittel*, SOEFW–Journal 122 p. 543, 545–546, 548 (1996).

Kosmetische Faerbemittel, Farbstoffkommission der Deutschen Forschungsgemeinschaft, Verlag Chemie, Weinheim, p. 81–106 (1984).

* cited by examiner

*Primary Examiner*—Sabiha Qazi
(74) *Attorney, Agent, or Firm*—John E. Drach; Steven J. Trzaska

(57) ABSTRACT

A hair treatment composition containing: (a) an esterquat; (b) an alkyl and/or alkenyl oligoglycoside; (c) a partial glyceride; and (d) a fatty alcohol ethoxylate.

8 Claims, No Drawings

HAIR-CONDITIONING AGENTS

BACKGROUND OF THE INVENTION

1. Field of the Invention

This invention relates to hair aftertreatment preparations containing esterquats, alk(en)yl glycosides and partial glycerides and to the use of the mixtures as hair treatment preparations.

2. Prior Art

As a result of frequent washing and shampooing and increased environmental influences, hair and particularly long hair is nowadays exposed to particularly severe stressing. Aftertreatment preparations containing hair care ingredients seek to remedy the situation. To this end, modern conditioners, treatments and rinses contain cationic surfactants, preferably those of the esterquat type, which provide the hair with a pleasant soft feel and which reduce static charging between the fibers so that combing work is reduced. Patent Application WO/97/47284 describes cosmetic hair care preparations of (a) esterquats, (b) sorbitan esters, (b2) polyol-12-hydroxystearates and/or (b3) glycerides and optionally alkyl polyglycosides and fatty alcohols. Although esterquats already have very favorable performance properties, there is still a need on the market for an improved performance profile. Accordingly, the problem addressed by the present invention was to provide hair aftertreatment preparations based on esterquats which would be distinguished in particular by improved feel properties.

DESCRIPTION OF THE INVENTION

The present invention relates to hair aftertreatment preparations containing (a) esterquats, (b) alkyl and/or alkenyl oligoglycosides, (c) partial glycerides and (d) fatty alcohol ethoxylates.

It has surprisingly been found that the addition of mixtures of alkyl and/or alkenyl oligoglucosides and partial glycerides considerably improves the feel properties of hair aftertreatment preparations containing esterquats as cationic surfactants. Mixtures of alkyl oligoglucosides and oleic acid monoglycerides marketed under the name of Lamesoft® PO 65 have proved to be particularly effective in this regard. The advantageous properties of the preparations can be further improved by the use of fatty alcohol ethoxylates.

Esterguats

"Esterquats" are generally understood to be quaternized fatty acid triethanolamine ester salts. These are known substances which may be obtained by the relevant methods of preparative organic chemistry, cf. International patent application WO 91/01295 (Henkel). According to this document, triethanolamine is partly esterified with fatty acids in the presence of hypophosphorous acid, air is passed through and the reaction product is quaternized with dimethyl sulfate or ethylene oxide. In addition, a process for the production of solid esterquats in which quaternization of triethanolamine esters is carried out in the presence of suitable dispersants, preferably fatty alcohols, is known from German patent DE-C1 4308794. Overviews on this subject have been published, for example, by R. Puchta et al. in Tens. Surf. Det., 30, 186 (1993), by M. Brock in Tens. Surf, Det. 30, 394 (1993), by R. Lagerman et al. in J. Am. Oil. Chem. Soc., 71, 97 (1994) and by I. Shapiro in Cosm. Toil, 109, 77 (1994). The quaternized fatty acid triethanolamine ester salts correspond to formula (I):

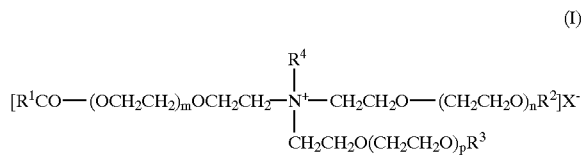

in which $R^1CO$ is an acyl group containing 6 to 22 carbon atoms, $R^2$ and $R^3$ independently of one another represent hydrogen or have the same meaning as $R^1CO$, $R^4$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained for example in the pressure hydrolysis of natural fats and oils. Technical $C_{12/18}$ cocofatty acids and, in particular, partly hydrogenated $C_{16/18}$ tallow or palm oil fatty acids and high-elaidic $C_{16/18}$ fatty acid cuts are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{12/18}$ tallow or palm oil fatty acid (iodine value 0 to 40). In performance terms, quaternized fatty acid triethanolamine ester salts corresponding to formula (I), in which $R^1CO$ is an acyl group containing 16 to 18 carbon atoms, $R^2$ has the same meaning as $R^1CO$, $R^3$ is hydrogen, $R^4$ is a methyl group, m, n and p stand for 0 and X stands for methyl sulfate, have proved to be particularly advantageous. Other suitable esterquats besides the quaternized fatty acid triethanolamine ester salts are quaternized ester salts of fatty acids with diethanolalkyamines corresponding to formula (II):

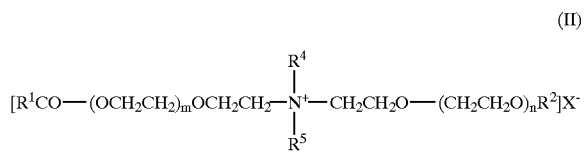

in which $R^1CO$ is an acyl group containing 6 to 22 carbon atoms, $R^2$ is hydrogen or has the same meaning as $R^1CO$, $R^4$ and $R^5$ independently of one another are alkyl groups containing 1 to 4 carbon atoms, m and n together stand for 0 or numbers of 1 to 12 and X stands for halide, alkyl sulfate or alkyl phosphate. Finally, another group of suitable esterquats are the quaternized ester salts of fatty acids with 1,2-dihydroxypropyl dialkylamines corresponding to formula (III):

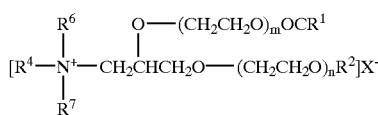

(III)

in which $R^1CO$ is an acyl group containing 6 to 22 carbon atoms, $R^2$ is hydrogen or has the same meaning as $R^1CO$, $R^4$, $R^6$ and $R^7$ independently of one another are alkyl groups containing 1 to 4 carbon atoms, m and n together stand for 0 or numbers of 1 to 12 and X stands for halide, alkyl sulfate or alkyl phosphate. So far the choice of the preferred fatty acids and the optimum degree of esterification is concerned, the examples mentioned in regard to (I) also apply to the esterquats of formulae (II) and (III). The esterquats are normally marketed in the form of 50 to 90% by weight alcoholic solutions which may readily be diluted with water as required.
Alkyl and/or alkenyl oligoglycosides Alkyl and alkenyl oligoglycosides are known nonionic surfactants which correspond to formula (IV:

(IV)

in which $R^8$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (IV) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view. The alkyl or alkenyl radical $R^8$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^8$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.
Partial Glycerides Partial glycerides, i.e. monoglycerides, diglycerides and technical mixtures thereof may still contain small quantities of triglycerides from their production. The partial glycerides preferably correspond to formula (V):

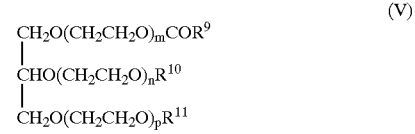

(V)

in which $R^9CO$ is a linear or branched, saturated and/or unsaturated acyl group containing 6 to 22 and preferably 12 to 18 carbon atoms, $R^{10}$ and $R^{11}$ independently of one another have the same meaning as $R^9CO$ or represent OH and the sum (m+n+p) is 0 or a number of 1 to 100 and preferably 5 to 25, with the proviso that at least one of the two substituents $R^{10}$ and $R^{11}$ is OH. Typical examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof. Technical lauric acid glycerides, palmitic acid glycerides, stearic acid glycerides, isostearic acid glycerides, oleic acid glycerides, behenic acid glycerides and/or erucic acid glycerides which have a monoglyceride content of 50 to 95% by weight and preferably 60 to 90% by weight are preferably used.
Fatty Alcohols and Fatty Alcohol Ethoxylates Fatty alcohols and fatty alcohol ethoxylates in the context of the present invention are primary aliphatic alcohols and ethylene oxide adducts thereof which correspond to formula (VI):

(VI)

in which $R^{12}$ is an aliphatic, linear or branched hydrocarbon radical containing 6 to 22 carbon atoms and 0 and/or 1, 2 or 3 double bonds and z is 0 or a number of 1 to 20. Typical examples of suitable fatty alcohols are caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats or oils or aldehydes from Roelen's oxosynthesis and as monomer fraction in the dimerization of unsaturated fatty alcohols. Technical fatty alcohols containing 12 to 18 carbon atoms such as, for example, coconut, palm, palm kernel and tallow alcohol are preferred. Suitable fatty alcohol ethoxylates are products of the addition of 1 to 20 and preferably 2 to 10 moles of ethylene oxide with the primary alcohols mentioned above, which may have both a narrow and a conventional broad homolog distribution from their production. Coconut fatty alcohol ethoxylates containing 1 to 5 moles of ethylene oxide are preferably used.
Hair Aftertreatment Preparations In one preferred embodiment of the invention, the hair aftertreatment preparations contain (a) 0.1 to 10, preferably 1 to 3% by weight esterquats, (b) 0.1 to 10, preferably 1 to 5% by weight alkyl and/or alkenyl oligoglycosides, (c) 0.1 to 10, preferably 1 to 5% by weight partial glycerides, (d) 1.0 to 10, preferably 1 to 5% by weight fatty alcohol ethoxylates and optionally (e) 0 to 10, preferably 1 to 5% by weight fatty alcohols, with the proviso that the quantities shown add up to 100% by weight with water and optionally other auxiliaries and additives.

Commercial Applications

The preparations according to the invention provide hair with a pleasant soft feel and reduce static charging. Accordingly, the present invention also relates to the use of mixtures containing (a) esterquats, (b) alkyl and/or alkenyl oligoglycbsides, (c) partial glycerides and optionally (d) fatty alcohol ethoxylates for the production of hair aftertreatment preparations.

Auxiliaries and Additives

The preparations according to the invention, for example hair conditioners,.hair rinses, hair treatments and the like, may contain mild surfactants, oil components, emulsifiers, superfatting agents, pearlizing waxes, stabilizers, consistency factors, thickeners, polymers, silicone compounds, biogenic agents, antidandruff agents, film formers, preservatives, hydrotropes, solubilizers, UV filters, perfume oils, dyes or the like.

Typical examples of suitable mild, i.e. particularly dermatologically safe, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Suitable oil components are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono/di/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, ring opening products of epoxidized fatty acid esters with polyols, silicone oils and/or aliphatic or naphthenic hydrocarbons.

Suitable emulsifiers are, for example, nonionic surfactants from at least one of the following groups:

(1) products of the addition of 2 to 30 mol of ethylene oxide and/or 0 to 5 mol of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 mol of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) adducts of 15 to 60 mol of ethylene oxide with castor oil and/or hydrogenated castor oil;

(5) polyol esters and, in particular, polyglycerol esters such as, for example, polyglycerol polyricinoleate, polyglycerol poly-12-hydroxystearate and polyglycerol dimerate. Mixtures of compounds from several of these classes are also suitable;

(6) products of the addition of 2 to 15 mol of ethylene oxide onto castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(8) mono-, di- and trialkyl phosphates and mono-, di- and/or tri-PEG-alkyl phosphates and salts thereof;

(9) wool wax alcohols;

(10) polysiloxane/polyalkyl polyether copolymers and corresponding derivatives;

(11) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol, and

(12) polyalkylene glycols.

The addition products of ethylene oxide and/or propylene oxide with fatty alcohols, fatty acids, alkyl phenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred.

Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable pearlizing waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxysubstituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

The consistency factors mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quatemized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, Amodimethicone, copolymers of adipic acid and dimethylamino-hydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers. In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clays minerals, Pemulen and alkyl-modified Carbopol types (Goodrich).

UV protection factors in the context of the invention are organic substances which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor and derivatives thereof, for example 3-(4-methylbenzylidene)-camphor;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid isopentyl ester, 2-cyano-3-phenylcinnamic acid-2-ethylhexyl ester (Octocrylene);

esters of salicylic acid, preferably salicylic acid-2-ethylhexyl ester, salicylic acid-4-isopropylbenzyl ester, salicylic acid homomenthyl ester;

derivatives of benzophenone, preferably 2-hydroxy-4-methoxybenzo-phenone, 2-hydroxy4-methoxy-4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone;

propane-1,3-diones such as, for example, 1-(4-tert.butylphenyl)-3-(4'-methoxyphenyl)-propane-1,3-dione.

Suitable water-soluble substances are 2-phenylbenzimidazole-5-sulfonic acid and alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione or 1-phenyl-3-(4'-isopropylphenyl)-propane-1,3-dione. The UV-A and UV-B filters may of course also be used in the form of mixtures. Besides the soluble substances mentioned, insoluble light-blocking pigments, i.e. finely dispersed metal oxides or salts, for example titanium dioxide, zinc oxide, iron oxide, aluminium oxide, cerium oxide, zirconium oxide, silicates (talcum), barium sulfate and zinc stearate, may also be used for this purpose. The particles should have a mean diameter of less than 100 nm, preferably between 5 and 50 nm and more preferably between 15 and 30 nm. They may be spherical in shape although ellipsoidal particles or other non-spherical particles may also be used. Besides the two above-mentioned groups of primary UV filters, secondary filters of the antioxidant type which interrupt the photochemical reaction chain initiated when UV radiation penetrates the skin may also be used. Typical examples of secondary UV filters are Superoxid-Dismutase, tocopherols (vitamin E) and ascorbic acids (vitamin C). Other suitable UV filters can be found in P. Finkel's review in S ÖFW-Journal 122, 543 (1996).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid.

Suitable perfume oils are the extracts of blossoms (lavender, rose, jasmine, neroli), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Suitable synthetic or semisynthetic perfume oils are Ambroxan, eugenol, isoeugenol, citronellal, hydroxycitronellal, geranoil, citronellol, geranyl acetate, citral, ionone and methyl ionone.

The dyes used may be selected from any of the substances which are approved and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the preparation. The preparations may be produced by standard cold or hot processes and are preferably produced by the phase inversion temperature method.

EXAMPLES

The following hair aftertreatment preparations were subjected to a half-head test. Feel, luster and combability were subjectively evaluated by a panel of six trained testers who evaluated the properties on a scale of (+)=satisfactory to (+++)=very good. The figures shown represent the average values of three series of measurements. Preparations 1 and 2 correspond to the invention while preparations C1 and C2 are intended for comparison.

TABLE 1

Hair aftertreatment preparations in the half-head test

| Composition/performance | 1 | 2 | C1 | C2 |
|---|---|---|---|---|
| Distearoylethyl Hydroxyethylmonium Methosulfate (and) Cetearyl Alcohol | 1.4 | 1.4 | — | 1.4 |
| Ceteareth-20 | 2.5 | — | — | — |
| Cetearyl Alcohol (and) Ceteareth-20 | — | 2.5 | 4.0 | — |
| Cetearyl Alcohol | 2.5 | — | — | 2.1 |
| Glyceryl Stearate | — | — | — | 0.5 |
| Hydrogenated Palm Glycerides | 0.5 | 0.5 | 0.5 | — |
| Coco Glucosides | 1.5 | 1.5 | — | 2.0 |
| Dicaprylyl Ether | — | 1.0 | — | 1.0 |

TABLE 1-continued

Hair aftertreatment preparations in the half-head test

| Composition/performance | 1 | 2 | C1 | C2 |
|---|---|---|---|---|
| Coco Glucoside (and) Glyceryl Oleate | 5.0 | 5.0 | — | — |
| Water | | to 100 | | |
| Feel wet hair | +++ | +++ | + | + |
| Combability wet hair | ++ | + | + | + |
| Feel dry hair | +++ | + | + | + |
| Luster dry hair | + | +++ | + | + |

What is claimed is:

1. A hair treatment composition comprising:
   (a) from about 0.1 to 10% by weight, based on the weight of the composition, of an esterquat;
   (b) an alkyl and/or alkenyl oligoglycoside;
   (c) a partial glyceride; and
   (d) a fatty alcohol ethoxylate.

2. The composition of claim 1 wherein the alkyl and/or alkenyl oligoglycoside is present in the composition in an amount of from 0.1 to 10% by weight, based on the weight of the composition.

3. The composition of claim 1 wherein the partial glyceride is present in the composition in an amount of from 0.1 to 10% by weight, based on the weight of the composition.

4. The composition of claim 1 wherein the fatty alcohol ethoxylate is present in the composition in an amount of from 1 to 5% by weight, based on the weight of the composition.

5. A process for treating hair comprising contacting the hair with a treatment composition containing:
   (a) from about 0.1 to 10% by weight, based on the weight of the composition, of an esterquat;
   (b) an alkyl and/or alkenyl oligoglycoside;
   (c) a partial glyceride; and
   (d) a fatty alcohol ethoxylate.

6. The process of claim 5 wherein the alkyl and/or alkenyl oligoglycoside is present in the composition in an amount of from 0.1 to 10% by weight, based on the weight of the composition.

7. The process of claim 5 wherein the partial glyceride is present in the composition in an amount of from 0.1 to 10% by weight, based on the weight of the composition.

8. The process of claim 5 wherein the fatty alcohol ethoxylate is present in the composition in an amount of from 1 to 5% by weight, based on the weight of the composition.

* * * * *